(12) United States Patent
LeCluyse et al.

(10) Patent No.: US 6,780,580 B2
(45) Date of Patent: Aug. 24, 2004

(54) METHOD OF SCREENING CANDIDATE COMPOUNDS FOR SUSCEPTIBILITY TO BILIARY EXCRETION

(75) Inventors: Edward L. LeCluyse, Chapel Hill, NC (US); Kim L. R. Brouwer, Chapel Hill, NC (US); Xingrong Liu, Groton, CT (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/527,352

(22) Filed: Mar. 17, 2000

(65) Prior Publication Data

US 2003/0044883 A1 Mar. 6, 2003

Related U.S. Application Data

(60) Provisional application No. 60/124,810, filed on Mar. 17, 1999.

(51) Int. Cl.[7] ............................. C12Q 1/00; C12N 5/08; C12N 5/06
(52) U.S. Cl. ......................... 435/4; 435/370; 435/366; 435/325
(58) Field of Search .......................... 435/4, 370, 366, 435/325

(56) References Cited

U.S. PATENT DOCUMENTS 5,602,026 A * 2/1997 Dunn et al. ................. 435/395

FOREIGN PATENT DOCUMENTS

WO      WO 94/12662     6/1994
WO      WO 96/01426     1/1996

OTHER PUBLICATIONS

LeCruse et al. Am. J. Physiol. 266 (Cell Physiol.35):C1764–C1774, 1994.*
Poole et al. Archives of Toxicology. (1990) 64:474–481.*
Liu et al., "Partial Maintenance of Taurocholate Uptake by Adult Rat Hepatocytes Cultured in a Collagen Sandwich Configuration," Pharmaceutical Research, vol. 15, No. 10, 1998. (Journal Article).
Liu et al., "Biliary Excretion of Taurocholate (TC) in Rat Hepatocytes Cultured in a Collagen Sandwich Configuration (SC)", Hepatology 24:370A (973), 1996, (Abstract).
Liu et al., "Biliary Excretion in Sandwich–Cultured (SC) Hepatocytes: A Novel In Vitro Model System for Investigating Biliary Excretion," Pharm. Sci. 1:S–119, 1998. (Abstract).
Liu et al., "Taurocholate (TC) Uptake in Rat Hepatocytes Cultured in a Collagen Sandwich Configuration (SC)," Pharm. Res. Init. 13:S–393 (8003), 1996. (Abstract).
Liu et al., "Prediction of In Vivo Biliary Excretion of Model Compounds from Hepatocytes Cultured in a Sandwich Configuration," Pharm. Res. 24:S–459 (3007), 1997. (Abstract).
Liu et al., "Hepatocytes Cultured in a Sandwich Configuration (SC) as an In Vivo Model of Biliary Excretion: Effects of Ca++ on Taurocholate (TC) Uptake and Retention," Hepatology 26:297A (675), 1997. (Abstract).
Liu et al., "Correlation of Biliary Excretion in Sandwich Cultured Rat Hepatocytes and In Vivo in Rats," Drug Metabolism and Disposition, vol. 27 (No. 6), p. 637–644, (1999).
Liu et al., "Use of Ca2+ Modulation to Evaluate Biliary Excretion in Sandwich–Cultured Rat Hepatocytes," Journal of Pharmacology and Experimental Therapeutics, vol. 289 (No. 3), p. 1592–1599, (1999).

* cited by examiner

Primary Examiner—Jon Weber
Assistant Examiner—Vera Afremova
(74) Attorney, Agent, or Firm—Jenkins, Wilson & Taylor, P.A.

(57) ABSTRACT

A method of screening a candidate compound for susceptibility to biliary excretion. The method includes the steps of providing a culture of hepatocytes, the culture having at least one bile canaliculus; exposing a candidate compound to the culture; and determining an amount of candidate compound in the at least one bile canaliculus, the amount of candidate compound in the at least one bile canaliculus indicating the susceptibility of the candidate compound to biliary excretion. Optionally, the culture of hepatocytes is a long-term culture in a sandwich configuration. The method is particularly applicable to the screening of multiple candidate compounds in a single effort.

14 Claims, 9 Drawing Sheets

METHOD OF SCREENING CANDIDATE COMPOUNDS FOR SUSCEPTIBILITY TO BILIARY EXCRETION

RELATED APPLICATION INFORMATION

This application claims the benefit of and priority to U.S. Provisional Patent Application No. 60/124,810, filed Mar. 17, 1999, the disclosure of which is incorporated herein by reference in its entirety.

GRANT STATEMENT

This invention was made in part from government support under Grant No. GM41935 from the National Institute of Health. Thus, the U.S. Government has certain rights in the invention.

TECHNICAL FIELD

The present invention relates to a method of screening compounds which are candidates primarily for use as therapeutic agents for susceptibility to biliary excretion. More particularly, the present invention relates to an in vitro method of screening candidate compounds for susceptibility to biliary excretion. Compounds can be chosen for use as therapeutic agents for administration to humans and other warm-blooded vertebrates.

| Table of Abbreviations | |
|---|---|
| AUC | area under the curve |
| BSEP | bile salt export pump |
| $Cl_B$ | biliary clearance |
| $Cl_{in}$ | intrinsic clearance |
| cMOAT | canalicular multispecific organic anion transporter |
| CFDA | carboxyfluorescein diacetate |
| DMEM | Dulbecco's modified Eagle's medium |
| EDTA | ethylenediamine tetraacetate |
| HP | Hewlett Packard |
| HPLC | high performance liquid chromatography |
| hr | hour |
| i.v. | intravenous |
| i.p. | intraperitoneal |
| $K_m$ | Michaelus-Menten constant for enzyme-substrate reaction |
| LC/MS | liquid chromatography/mass spectrometry |
| mg pr. | milligrams protein |
| min | minute |
| MDR2 | multidrug resistance protein 2 |
| MRP2 | multidrug resistance associated protein 2 |
| Ntcp | Na$^+$/taurocholate cotransporting polypeptide |
| OATP1 | organic ion anion transporting polypeptide 1 |
| OATP2 | organic ion anion transporting polypeptide 2 |
| P-gp | P-glycoprotein |
| SD | standard deviation |
| UV | ultraviolet |
| UV/VIS | ultraviolet/visible |
| $V_{max}$ | maximum velocity of enzyme-catalyzed reaction |

BACKGROUND ART

First-pass metabolism pertains to the absorption of therapeutic agents, drugs or other compounds into the portal blood supply that leads to the liver. When a drug is swallowed, the stomach and small intestine absorb it, with subsequent flow in the blood to the portal vein entry to the liver. The liver may then in turn rapidly absorb and metabolize the drug at high concentrations through the liver blood supply. Thus, large amounts of the drug may never be seen by the systemic circulation or drug effect site. Additionally, rapid metabolism via the first-pass metabolism route can lead to the formation of high plasma concentrations of unwanted metabolites.

Thus, in the liver, therapeutic compositions are often undesirably removed from an animal's circulatory system in that they are taken up by hepatocytes (liver cells) and excreted in bile via the bile canaliculi. Uptake into the hepatocytes is mediated by transport systems endogenous to hepatocytes, including Ntcp and cMOAT. Such transporters move xenobiotics like therapeutic compositions as well as endogenous compounds across the sinusoidal membrane of the hepatocytes. Bile canaliculi are structures within liver tissue that receive excreted components from the hepatocytes and transport the bile to a common bile duct for removal from the animal. Biliary excretion of substrates is thus a complex process involving translocation across the sinusoidal membrane, movement through the cytoplasm, and transport across the canalicular membrane.

The advent of combinatorial chemistry techniques has enabled the identification of extremely high numbers of compounds that have potential as therapeutic agents. However, assays for susceptibility to biliary excretion that can rapidly identify those candidate compounds that have a lower potential for uptake by hepatocytes and excretion through bile canaliculi have lagged behind the pace of synthesis and screening of pharmacological activities. Numerous in vivo (e.g. bile duct cannulated animals) and in vitro preparations (e.g. isolated perfused livers, isolated hepatocytes, hepatocyte couplets, liver plasma membrane vesicles and expressed transport proteins) have been used to investigate biliary excretion processes. See e.g. Oude Elferink et al., *Biochim. Biophys. Acta* 1241:215–268, 1995.

Additionally, short-term (3–8 hour) cultured hepatocyte couplets have been employed to examine directly the biliary excretion of fluorescent compounds utilizing fluorescence microscopy, as described by Graf and Boyer, *J. Hepatol.* 10:387–394,1990. However, the application of cultured hepatocyte couplets to study biliary excretion of xenobiotics is limited in that the substrate must contain a fluorescent chromophore.

Long-term (typically more than 24 hour) cultured hepatocytes have been reported to restore polarity with canalicular-like structures. See e.g., Barth and Schwarz, *Proc. Natl. Acad. Sci.* 79:4985–4987, 1982; Maurice et al., *J. Cell Sci.* 90:79–92, 1988; Talamini et al., *Hepatology* 25:167–172, 1997. Although primary hepatocytes maintained under conventional culture conditions have been used to study drug metabolism and hepatotoxicity, long-term cultures of hepatocytes have not been a suitable model for studying hepatobiliary transport. Particularly, as described by Groothuis and Meijer, *J. Heptaology* 24(Suppl. 1):3–28, 1996 and LeCluyse et al., *Adv. Drug Del. Rev.* 22:133–186, 1996, rapid loss of liver-specific function, including hepatic transport properties, and failure to establish normal bile canalicular networks and to maintain normal hepatocyte morphology have been observed in such cultures.

Existing methods have not been demonstrated to be widely applicable to investigate human biliary excretion. In addition, existing approaches cannot be used to examine efficiently biliary excretion processes for a large number of drug candidates. Thus, there is a long-felt need for an assay to assess susceptibility of candidate compounds for hepatic uptake and biliary excretion. Such an assay would facilitate elimination of those compounds with an undesirably high susceptibility for biliary excretion from further evaluation as therapeutic agents early in the evaluation process. Correspondingly, there is a long-felt need for the rapid identification of suitable candidate compounds (i.e., compounds that are not susceptible to biliary excretion) for further testing as therapeutic agents.

SUMMARY OF THE INVENTION

A method of screening a candidate compound for susceptibility to biliary excretion is disclosed herein. The method comprises the steps of providing a culture of hepatocytes, the culture comprising at least one bile canaliculus having a canalicular space; exposing a candidate compound to the culture; and determining an amount of the candidate compound in the canalicular space of the at least one bile canaliculus, the amount of the candidate compound in the canalicular space of the at least one bile canaliculus indicating the susceptibility of the candidate compound to biliary excretion. The culture of hepatocytes preferably comprises a long-term culture in a sandwich configuration.

Accordingly, it is an object of the present invention to provide a rapid and inexpensive method of screening of candidate compounds for susceptibility to biliary excretion.

It is a further object of the present invention to provide an in vitro method of screening candidate compounds for susceptibility to biliary excretion.

It is yet a further object of the present invention to provide a method of screening candidate compounds for susceptibility to biliary excretion which facilitates the screening of many candidate compounds in a single effort.

It is still a further object of the present invention to provide a high throughput method of screening of candidate compounds for susceptibility to biliary excretion.

Some of the objects of the invention having been stated herein above, other objects will become evident as the description proceeds, when taken in connection with the accompanying Laboratory Examples and Drawings as best described herein below.

DETAILED DESCRIPTION OF THE INVENTION

Figure 1A:
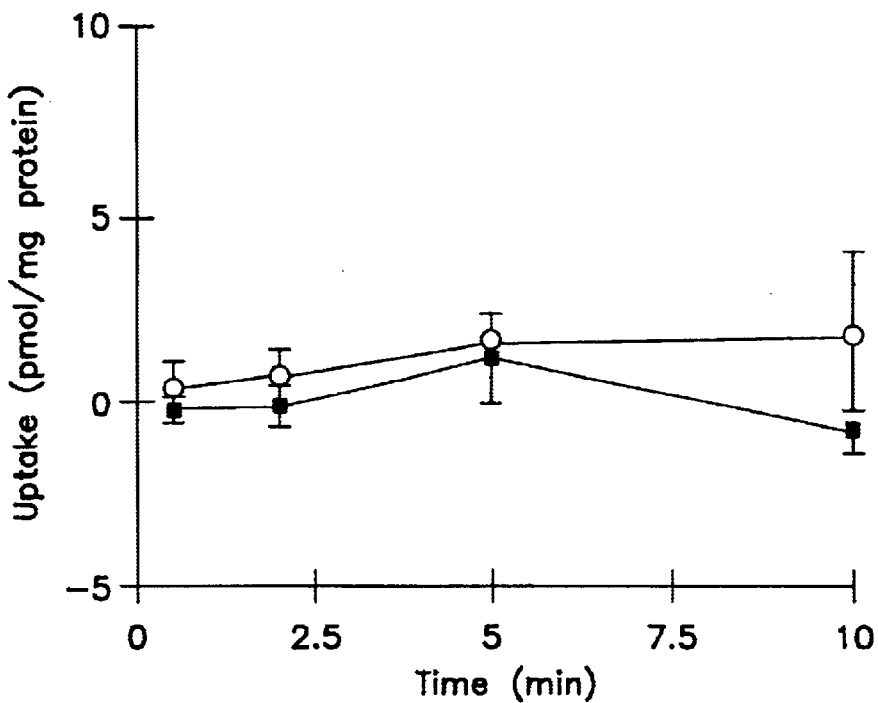
FIG. 1A is a graph depicting cumulative uptake of [$^3$H] inulin (1 $\mu$M) in standard buffer (closed symbols) and $Ca^{++}$-free buffer (open symbols) in hepatocyte monolayers cultured for 3 hr.

In accordance with the present invention, a method is provided for the screening of a candidate compound or substrate for susceptibility to biliary excretion. The method comprises the steps of providing a culture of hepatocytes, the culture comprising at least one bile canaliculus having a canalicular space; exposing a candidate compound to the culture; and determining an amount of the candidate compound in the canalicular space of the at least one bile canaliculus, the amount of the candidate compound in the canalicular space of the at least one bile canaliculus indicating the susceptibility of the candidate compound to biliary excretion.

As would be appreciated by one of ordinary skill in the art, in vivo biliary excretion of substrates involves translocation across the sinusoidal membrane, movement through the cytoplasm, and transport across the canalicular membrane. Thus, in a preferred hepatocyte culture of the present invention, functional properties displayed by hepatocytes in vivo are established. For example, the establishment of hepatic transport systems, such as sinusoidal or canalicular transport systems, or both sinusoidal and canalicular transport systems is particularly contemplated in accordance with the present invention. Exemplary transport systems include, but are not limited to, Ntcp, cMOAT, OATP1, OATP2, MRP2, P-gp, BSEP and MDR2.

Additionally, the establishment of at least one bile canaliculus and the establishment of normal hepatocyte morphology in the hepatocyte cultures are also contemplated in accordance with the present invention. Preferably, the culture comprises a plurality of bile canaliculi. More preferably, the plurality of bile canaliculi comprise a canalicular network. The amount of candidate compound, as discussed in detail below, in the canalicular space of the at least one bile canaliculus indicates the susceptibility of the candidate compound to biliary excretion.

While the following terms are believed to be well understood by one of ordinary skill in the art, the following definitions are set forth to facilitate explanation of the invention.

The term "candidate compound" or "candidate substrate" is meant to refer to any compound wherein the characterization of the compound's susceptibility to biliary excretion is desirable. Exemplary candidate compounds or substrates include xenobiotics such as drugs and other therapeutic agents, carcinogens and environmental pollutants, as well as endobiotics such as steroids, fatty acids and prostaglandins.

The candidate drugs and other therapeutic agents screened in accordance with the method of the present invention are contemplated to be useful in the treatment of warm-blooded vertebrates. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

The term "biliary excretion" is meant to refer to a biological process wherein substances are removed from an animal's circulatory system by being taken up by hepatocytes (liver cells) and excreted in bile via the bile canaliculi. Uptake into the hepatocytes is mediated by transport systems endogenous to hepatocytes, including, but not limited to, Ntcp and OATP1. Bile canaliculi are structures within liver tissue which receive excreted components from the hepatocytes and transport the bile to a bile duct for removal from the animal.

By the phrase "an amount of candidate compound" and/or the phrase "determining an amount of candidate compound in the at least one bile canaliculus", as used herein and in the claims, it is meant to refer to any amount of candidate compound that is taken up by hepatocytes and excreted into the at least one bile canaliculus in accordance with the assay of the present invention. For example, "an amount" can refer to substantially no candidate compound residing in the at least one bile canaliculus after exposure of a candidate compound to a culture in accordance with the present invention. Alternatively, "an amount" can refer to substantially all of the candidate compound residing in the at least one bile canaliculus after exposure of a candidate compound to a culture in accordance with the present invention. Thus, the phrase "an amount of candidate compound in the at least one bile canaliculus" can be used to describe candidate compounds that are not highly excreted, extensively excreted, and extensively and rapidly excreted.

The phrase "determining an amount of candidate compound in the at least one bile canaliculus" is also meant to refer to the use of a biliary excretion index calculation and a biliary clearance calculation as described herein below. The phrase "determining an amount of a candidate compound in the at least one bile canaliculus" may also refer to the detection of a reduced amount of a marker compound due to uptake of candidate compound into the at least one bile canaliculus as described in the high throughput embodiment of the assay of the present invention described herein below. Thus, quantitative and qualitative determinations of "an amount of candidate compound in the at least one bile canaliculus" are contemplated to be within the scope of the present invention.

The phrase "an amount of candidate compound" and/or the phrase "determining an amount of candidate compound in the at least one bile canaliculus" are also meant to refer to the screening of, for example, a class or series of candidate compounds and then establishing a ranking of susceptibility to biliary excretion of the candidate compounds within the class or series. It is thus contemplated in accordance with a preferred embodiment of the present invention that the candidate compound or compounds wherein lesser or lower susceptibility to excretion is observed according to such a ranking may be chosen for further experimentation or development as a therapeutic agent, while compounds wherein higher or greater susceptibility to excretion is observed according to such a ranking may be excluded from further experimentation or development as a therapeutic agent.

However, as would be readily apparent to one of ordinary skill in the art, the characteristic that a compound is susceptible to biliary excretion does not necessarily preclude further development of the compound as a therapeutic agent. Indeed, the decision of whether to proceed with the development of a particular candidate compound as a therapeutic agent is based on many factors, including, but not limited to, the biological activity of the candidate compound. While susceptibility to biliary excretion is an important factor, it is not the only factor that is typically considered by one of ordinary skill in the art. Characterization of susceptibility to biliary excretion in accordance with the method of the present invention thus provides data that is desirable for use by one of ordinary skill in the art in evaluating whether to proceed with the development of a candidate compound as a therapeutic agent.

The term "marker compound" is meant to refer to a chemical compound that is readily detectable using a standard detection technique, such as fluorescence or chemiluminescence spectrophotometry, scintillation spectroscopy, chromatography, liquid chromatography/mass spectroscopy (LC/MS), colorimetry, and the like. Exemplary marker compounds thus include, but are not limited to, fluorogenic or fluorescent compounds, chemiluminescent compounds, calorimetric compounds, UV/VIS absorbing compounds, radionuclides and combinations thereof.

Therapeutic compositions that are taken up and excreted extensively though the biliary excretion processes described herein typically have a minimal chance of imparting therapeutic effects in a subject. It is thus very desirable to establish an in vitro test for a compound's susceptibility to hepatocyte uptake and biliary excretion so as to facilitate elimination of a compound with an undesirably high susceptibility from further evaluation as a therapeutic agent early in the evaluation process. The biliary excretion assay of the present invention provides such a test.

Rat hepatocytes are preferred in a culture for use in the method of the present invention; but, any suitable source of hepatocytes as would be apparent to one of ordinary skill in the art is contemplated to be within the scope of the present invention. Exemplary sources include the warm-blooded vertebrates listed above. In particular, exemplary sources include, but are not limited to, human beings, monkeys, apes, cats, dogs, pigs, hogs, cattle, oxen, sheep, horses, turkeys, chickens, ducks and geese.

The biliary excretion assay method of the present invention may optionally comprise establishing a sandwich culture of hepatocytes wherein at least one hepatocyte layer is formed between two layers of matrix. While configuration as a sandwich culture is the preferred configuration for the culture, any suitable configuration as would be apparent to one of ordinary skill in the art is contemplated to be within the scope of the present invention. For example, clusters, aggregates or other associations or groupings of hepatocytes in a culture wherein at least one bile canaliculus is formed and wherein functional properties of hepatocytes are established are contemplated to fall within the scope of the present invention. Preferably, the culture configuration facilitates the formation of a plurality of bile canaliculi. More preferably, the culture configuration facilitates the formation of a canalicular network. The amount of candidate compound, as discussed in detail herein, in the canalicular space of the bile canaliculi indicates the susceptibility of the candidate compound to biliary excretion.

Additionally, in the preferred sandwich configuration, hepatocytes are cultured in monolayers between two layers of matrix or scaffolding. But, the hepatocytes can also be embedded in the matrix or can extend non-uniformly through the matrix vertically, horizontally, diagonally, or in any combination thereof, such that one-dimensional, two-dimensional and three-dimensional hepatocytes aggregates are formed. In accordance with the present invention, it is thus contemplated that the hepatocyte cultures can be formed by mixing hepatocyte cells with an appropriate matrix and inserting the mixture into a suitable culture container, such as a multi-well plate.

While collagen is a preferred substrate or scaffolding for the culture of hepatocytes, any suitable substrate or scaffolding whether natural, synthetic or combinations thereof as would be apparent to one of ordinary skill in the art is contemplated to be within the scope of the present invention. For example, other biological substrates, including but not limited to laminin and the basement membrane derived biological cell culture substrate sold under the registered trademark MATRIGEL® by Collaborative Biomedical Products, Inc. of Bedford, Mass., are contemplated to comprise suitable substrate or scaffolding material. Synthetic matrix materials, substrate materials or scaffolding materials, which are typically made from a variety of materials such as polymers, are also contemplated to fall within the scope of the present invention. The variation of component materials with a particular matrix for use in culturing hepatocytes is also contemplated in accordance with the method of the present invention.

The cultured hepatocytes are preferably cultured as a "long-term culture". By "long-term culture" it is meant to refer to hepatocytes that have been cultured for at least about 12 hours. More preferably, by "long-term culture" it is meant to refer to hepatocytes that have been cultured for at least about 24 hours, for at least about 48 hours, or for at least about 72 hours. Even more preferably, by "long-term culture" it is meant to refer to hepatocytes that have been cultured for at least about 96 hours. Long-term culturing facilitates the formation of bile canaliculi and the establishment of functional properties within the hepatocytes.

Following long-standing patent law convention, the terms "a" and "an" mean "one or more" when used in this application, including the claims.

Side-by-Side Embodiment

In accordance with one embodiment of the present invention, replicate hepatocyte cultures are established, preferably in sandwich configuration. A first culture is exposed to a standard buffer and a second culture is exposed to a $Ca^{++}$-free buffer. Exposure to the $Ca^{++}$-free buffer disrupts the bile canaliculi within the hepatocyte monolayers by breaking down adhesional processes or junctional complexes in the monolayer of hepatocytes. While exposure to the $Ca^{++}$-free buffer is a preferred method of breaking down the adhesional processes or junctional complexes to substantially disrupt the bile canaliculi, any suitable technique for breaking down the adhesional processes or junctional complexes to promote substantial disruption of the bile canaliculi as would be apparent to one of ordinary skill in the art is contemplated to be within the scope of the present invention. Exemplary techniques include, but are not limited to, the administration to the culture of peptides which interact with cell-to-cell binding sites to thereby prevent neighboring cells from binding.

A candidate compound or compounds is/are then added to each culture. The candidate compound(s) cannot be retained within the bile canaliculi in the culture that was treated with $Ca^{++}$-free buffer. Thus, in this culture, candidate compound (s) may be taken up into the hepatocytes and retained within the cytoplasm of the hepatocytes. However, any amount of the candidate compound(s) that is excreted by the hepatocytes across the canalicular membrane will flow into the buffer medium and will be removed when the buffer medium is removed. In contrast, when candidate compound(s) is/are administered to the hepatocyte sandwich culture in which the bile canaliculi are intact, any candidate compound(s) that is/are taken up by the cells and excreted by the cells is/are maintained both in the cytoplasm of the hepatocytes and in the bile canaliculi.

It is then desirable to obtain a measurement of the amount of candidate compound present within the intact bile canaliculi. The buffer media is removed from the cultures and the cultures are washed and lysed. As described in the Laboratory Examples presented herein below, the lysing of the cells within the cultures may be accomplished by addition of a suitable lysis buffer coupled with agitation of the culture. A preferred lysis buffer includes a detergent. The desired measurement is obtained by comparing the amount of candidate substance present in the lysate from the culture which has disrupted bile canaliculi (such as by exposure to $Ca^{++}$-free medium) as compared to the lysate from the culture with intact bile canaliculi. Two particular calculations have been utilized to compare the cultures and to determine an amount of the candidate compound residing in the intact bile canaliculi. As described above, the amount of candidate compound in the intact bile canaliculi indicates the candidate compound's susceptibility to biliary excretion.

One calculation is described as a biliary excretion index, which is a calculation of the uptake and excretion of the candidate compound as follows: 100%×{(uptake in the culture with intact bile canaliculi minus uptake within hepatocytes only in the $Ca^{++}$-free culture) divided by (uptake in the culture with intact bile canaliculi)}. The other calculation is a biliary clearance calculation, which is performed as follows: (uptake in the culture with intact bile canaliculi minus uptake within hepatocytes only in the $Ca^{++}$-free culture) divided by (time of incubation multiplied by the concentration of the candidate compound in the buffer medium).

Upon comparison of the in vitro assay of the present invention to a standard in vivo assay for biliary excretion as described in the Laboratory Examples presented herein below, it was determined that biliary clearance provided a more accurate and desirable evaluation of excretion. Particularly, the in vitro biliary clearance calculation adequately differentiated among candidate substances that are: (1) not highly excreted; (2) extensively excreted; and (3) extensively and rapidly excreted. Thus, the use of the biliary clearance calculation comprises an important aspect of the invention.

Metabolite Assay Embodiment

In the hepatocytes of the method of the present invention certain metabolic activities (called Phase I activities) may be substantially reduced. The substantial reduction in metabolic activity coupled with maintenance of biliary transport represents an advantage of the in vitro biliary excretion assay of the present invention in that a differentiation can be made between biliary excretion of a parent candidate compound versus a metabolite or metabolites of the parent candidate compound. This feature comprises an important aspect of the present invention.

In accordance with a preferred embodiment of the metabolite assay of the present invention, the method comprises establishing a first set and second set of two cultures of hepatocytes, with each culture preferably comprising at least one layer of hepatocytes sandwiched between two layers of collagen and at least one bile canaliculus formed within at least one layer of hepatocytes. The first set of cultures includes intact bile canaliculi and the second set of cultures includes disrupted bile canaliculi.

Metabolic enzyme activity and/or transport systems are then induced in the hepatocytes of one of the cultures within each of the first set and second set of cultures in accordance with art-recognized techniques using inducers which are known to up-regulate Phase I hepatic enzyme activity, such as phenobarbital and β-naphthoflavone. Exemplary inducers and techniques associated with the same are described by Parkinson, A. (1996) *Biotransformation of Xenobiotics in Casarett and Doull's Toxicology. The Basic Science of Poisons.*, $5^{th}$ Ed. (Klaassen, C. D. ed.) pp. 113–186, McGraw Hill, N.Y., and by LeCluyse et al., (1996) *Cultured rat hepatocytes, in Models for Assessing Drug Absorption and Metabolism* (Borchard et al. eds), pp 121–160, Plenum Press, New York, the contents of each of which are herein incorporated by reference.

A candidate parent compound is exposed to the first and second sets of cultures for a time sufficient to allow uptake of the candidate parent compound. Each set of cultures is washed and then lysed. The amount of candidate parent compound present in the lysate obtained from the culture in each set of cultures having inactive metabolic enzymes is determined. The amount of metabolite of the candidate parent compound present in the lysate obtained from the culture in each set of cultures having active metabolic enzymes is also determined.

A biliary clearance value for the cultures having inactive metabolic enzymes is calculated using the amount of candidate parent compound in the culture lysate. The calculated biliary clearance value is then used to determine the susceptibility of the candidate parent compound to biliary excretion, as described above. A biliary clearance value for the cultures having active metabolic enzymes is calculated using the amount of metabolite of the candidate parent compound in the culture lysate. The calculated biliary clearance value is then used to determine the susceptibility of the metabolite to biliary excretion, as described above. This information is contemplated to be useful, for example, in evaluating whether or not to administer a therapeutic composition in a pro-drug form.

High Throuqhput Assay Embodiment

An additional alternative embodiment of the present invention pertains to a high throughput hepatic uptake and biliary excretion assay. Such an assay preferably involves the use of cultured hepatocytes as described above, in conjunction with a marker compound that is a substrate for endogenous sinusoidal or canalicular transport systems, or both sinusoidal and canalicular transport systems. Exemplary transport systems include, but are not limited to, Ntcp, cMOAT, OATP1, OATP2, MRP2, P-gp, BSEP and MDR2. Particularly, a candidate compound is administered to a hepatocyte culture in conjunction with a marker compound in accordance with the cell culture and compound administration techniques described in the Laboratory Examples presented below.

Uptake and excretion competition between a candidate compound and the marker compound is then evaluated. That is, a significant drop in the amount of marker compound (e.g. measured or detected signal from the marker compound) within bile canaliculi in a culture may indicate that the candidate compound (as opposed to the marker compound) is taken up and excreted extensively.

A ranking of susceptibility to hepatic uptake and biliary excretion of the candidate compounds is then established. It is thus contemplated in accordance with a preferred embodiment of the high throughput assay of the present invention that the candidate compound or compounds wherein lesser or lower susceptibility to excretion is observed according to such a ranking may be chosen for further experimentation or development as a therapeutic agent, while compounds wherein higher or greater susceptibility to excretion is observed according to such a ranking may be excluded from further experimentation or development as a therapeutic agent.

An exemplary marker compound comprises the fluorescent cMOAT/MRP2 substrate, carboxydichlorofluorescein.

Preferably, carboxydichloroflorescein diacetate, which exhibits only a weak fluorescence, is utilized as a fluorogenic precursor due to its rapid penetration into the hepatocyte plasma membrane. Carboxydichlorofluorescein diacetate is hydrolyzed readily in the cytoplasm of hepatocytes by intracellular esterases to a highly fluorescent product, carboxydichlorofluorescein as described in Haugland, *Molecular Probes: Handbook of Fluorescent Probes and Research Chemicals* (1992–1994), p. 134, Molecular Probes, Inc., 1992.

The fluorescence of carboxydichlorofluorescein is sensitive to pH and thus any assay based on the intensity of carboxydichlorofluorescence should consider the effects of pH. However, it has been observed that less than a 0.3 pH unit difference has been found between cytosol and bile canaliculi in hepatocyte couplets. Although carboxydichlorofluorescein has been used for pH determinations in acidic organelles, its fluorescence intensity is not altered markedly between pH 7.1 and pH 7.4. The fluorescence of carboxydichlorofluorescein at pH 7.4 is only about 10–20% higher than at pH 7.1 at maximum emission wavelength. Inasmuch as the fluorescence of carboxydichlorofluorescein is used as a qualitative probe to localize carboxydichlorofluorescein cellular distribution, the slight pH gradient between cytosol and the canaliculi do not affect the application of the high throughput assay of the present invention.

Additional marker compounds include, but are not limited to, fluorescein-labeled taurocholate, a bile acid that is rapidly and extensively taken up by hepatocytes and excreted into the bile canaliculi as described in the Laboratory Examples presented herein below; cholylglycylamido fluorescein, another fluorescent bile acid described by Boyer and Soroka, *Gastroenterology* 109:1600–1611 (1995); rhodamine 123 for MDR2 and P-gp; and carboxyfluorescein diacetate (CFDA).

It is contemplated that the method of the present invention may be performed within standard multi-well assay plates as are well known in the art, such as the 96-well micro-titer plates that are available from ICN Pharmaceuticals, Inc. (Costa Mesa, Calif.). Thus, a plurality of candidate compounds can be simultaneously screened for susceptibility to biliary excretion within multiple wells of a multi-well plate.

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Examples

The following Laboratory Examples pertain to the establishment of a correlation of biliary excretion in sandwich-cultured rat hepatocytes (present method) and in vivo in rats (standard). Five model substrates representing a diverse spectrum of biliary excretion properties were selected to examine the relationship between the percentage of the dose excreted in bile in vivo in rats and in vitro using sandwich-cultured hepatocytes in accordance with the methods of the present invention. The five model substrates included inulin, salicylate, methotrexate, [D-pen$^{2,5}$]enkephalin and taurocholate.

Additionally, a comparison of in vivo and in vitro biliary excretion of 264W94 and its metabolites is set forth in Example 4. Compound 2169W94 is the O-demethylated metabolite of 264W94 in rats and humans, which can undergo further conjugation with urindine-5'-diphosphoflucuronic acid to form a glucuronide conjugate (Silveret al., *ISSX Proceedings,* (San Diego, Calif. USA) pp. 387, 1996). The structural formulas of compounds 264W94 and 2169W94 are presented in FIG. 9.

Materials and Methods Used in the Examples

Chemicals. [$^3$H]Taurocholate (3.4 Ci/mmol; purity>97%), -[$^{14}$C]salicylate (55.5 mCi/mmol; purity>99%), and [$^3$H][D-pen$^{2,5}$]enkephalin (36 Ci/mmol; purity>97%0 were obtained from Dupont New England Nuclear (Boston, Mass.). [$^3$H]Methotrexate (13.7 Ci/mmol; purity>99%) and [$^3$H]inulin (1.3 Ci/mmol; purity 97%) were obtained from Amersham International plc (Buckinghamshire, England). Compounds [$^{14}$C]264W94 ((3R,5R)-3-butyl-3-ethyl-2,3,4,5-tetrahydro-7,8-dimethoxy-5-phenyl-1,4-benzothiazepine-1,1-dioxide; 45.5 mCi/mmol; purity>99%) and [$^{14}$C]2169W94 ((3R, 5R)-3-ethyl-2,3,4,5-tetrahydro-7-methoxy-8-hydroxy-5-phenyl-1, 4-benzothiazepine-1,1-dioxide; 43.7 mCi/mmol; purity>99%) were obtained from Glaxo Wellcome, Inc. (Research Triangle Park, N.C.). Collagenase (type I, class I) was obtained from Worthington Biochemical Corp. (Freehold, N.J.). Dulbecco's modified Eagles's medium (DMEM), fetal bovine serum and insulin were purchased from Gibco (Grand Island, N.Y.). Rat tail collagen (type I) was obtained from Collaborative Biomedical Research (Bedford, Mass.). All other chemicals and reagents were of analytical grade and were readily available from commercial sources.

Animals. Male Wistar rats (250–280 g) from Charles River Laboratory (Raleigh, N.C.) were used as liver donors. Rats were housed individually in stainless-steel cages in a constant alternating 12-hr light and dark cycle at least 1 week before the study was performed, and were fed ad libitum until use. Bile duct cannulated rats (200–250 g) were obtained from Charles River (Raleigh, N.C.). All procedures were approved by the Institutional Animal Care and Use Committee at the University of North Carolina at Chapel Hill, Chapel Hill, N.C.

Preparation of Culture Dishes. Plastic culture dishes (60 mm) were precoated with rat tail collagen at least 1 day prior to preparing the hepatocyte cultures. To obtain a gelled collagen substratum, ice-cold neutralized collagen solution (0.1 ml, 1.5 mg/ml, pH 7.4) was spread onto each culture dish. Freshly coated dishes were placed at 37° C. in a humidified incubator for approximately 1 hr to allow the matrix material to gel, followed by addition of 3 ml DMEM to each dish and storage in a humidified incubator.

Culture of Rat Hepatocytes. Hepatocytes were isolated with a two-step perfusion method. Briefly, rats were anesthetized with ketamine and xylazine (60 and 12 mg/kg i.p., respectively) prior to portal vein cannulation. The liver was perfused in situ with oxygenated Ca$^{2+}$-free Krebs-Henseleit bicarbonate buffer containing collagenase type I (0.5 mg/ml) for 10 min. The hepatic capsule was removed with forceps. The hepatocytes were released by shaking the liver gently in 100 ml DMEM.

The released cells were filtered through a sterile nylon mesh (70-$\mu$m). The hepatocyte suspensions were centrifuged at 50× g for 3 min. The cell pellet was resuspended in 25 ml DMEM and an equal volume of 90% isotonic polyvinylpyrrolidone-coated silica colloid centrifugation medium (pH 7.4) sold under the registered trademark PERCOLL® by Pharmacia, Inc. of Piscataway, N.J. The resulting cell suspension was centrifuged at about 70 to about 150× g for 5 min. The pellet was resuspended in 50 ml DMEM and the cell suspensions were combined into one tube followed by centrifugation at 50× g for 3 min. Hepatocyte viability was determined by trypan blue exclusion. Only those hepatocyte preparations with viability greater than 90% were utilized for further studies.

Hepatocyte suspensions were prepared with DMEM containing 5% fetal calf serum, 1 µM dexamethasone and 4 mg/L insulin. Hepatocyte suspensions were added to the precoated dishes at a density of about 2–3×10$^6$ cells/60-mm dish. Approximately 1 hr after plating the cells, the medium was aspirated and 3-ml fresh DMEM was added. For transport studies, hepatocytes that had been seeded for 3–5 hr without collagen overlay were defined as 3-hr or short-term cultured hepatocytes.

To prepare sandwich-cultured hepatocytes, neutralized collagen solution (0.1 ml, about 1.5 to about 3.0 mg/ml, pH 7.4) was added to the monolayers 24 hr after the cells were seeded. Cultures with collagen overlay were incubated for 45 min at 37° C. in a humidified incubator to allow the collagen to gel before addition of DMEM. Medium was changed on a daily basis until the fourth day after the cells were seeded. These hepatocytes were referred to as 96-hr or long-term cultured hepatocytes.

Cumulative Uptake Studies in Sandwich-Cultured Hepatocytes. Hepatocytes cultured in a collagen-sandwich configuration were incubated in 3 ml standard buffer or Ca$^{2+}$- free buffer at 37° C. for 10 min. After removing the incubation buffer, uptake was initiated by addition of 3 ml standard buffer containing substrate to each dish. After incubation for designated times, cumulative uptake was terminated by aspirating the incubation solution and rinsing 4 times with 3 ml ice-cold standard buffer to remove extracellular substrate. After washing, 2 ml of 1% Triton X-100 solution was added to culture dishes, and the cells were lysed by shaking the dish on a shaker for 20 min at room temperature. An aliquot (1 ml) of lysate was analyzed by liquid scintillation spectrometry. Bio-rad DC Protein Assay Kit (Bio-Rad Laboratories, Hercules, Calif.) was used to determine the protein concentration in the culture extracts using bovine serum albumin as standard. Triton X-100 (1%) did not interfere with the assay. All values for substrate uptake into cell monolayers were corrected for nonspecific binding to the collagen by subtracting the substrate uptake determined in the appropriate control dishes in the absence of cells as described previously.

Biliary Excretion in Rats after Intravenous Administration of 264W94 and Oral Administration of 2169W94. [$^{14}$C] 264W94 was formulated as a solution in a mixture of sterile water/polypropylene glycol 400/ethanol (2:1:1 v/v/v) at a concentration of 0.125 mg/mL. Following collection of pre-dose bile, [$^{14}$C]264W94 solution was administrated by caudal vein injection (0.1 mg/kg). For the 2169W94 studies, [$^{14}$C]2169W94 was prepared as a suspension at a concentration of 0.1 mg/mL in 0.5% (w/v) methylcellulose in water. Following collection of pre-dose bile, [$^{14}$C]2169W94 suspension was administrated by gavage (1.0 mg/kg). All rats were placed into individual plastic metabolism cages that allowed the rats unrestrained movement. Bile was collected into polypropylene containers surrounded by ice. For the 264W94 studies, the bile container was changed at 8 and 24 hours after the dose. Previous studies indicated that samples were stable on ice for 24 hours. Bile samples were stored at −20° C. until analysis.

Analytical Procedure. Aliquots of cell lysate or bile samples containing 264W94 or 2169W94 were mixed with 2-fold volumes of ice-chilled acetonitrile, and centrifuged to remove precipitated proteins. The supernatant was evaporated under nitrogen at room temperature, and reconstituted in 100 µL of a 70/30 mixture of 50 mM ammonium acetate/acetonitrile/trifluoroacetic acid (95:5:0.1 v:v:v) and acetonitrile. The sample extracts were injected onto a WATERS™ SYMMETRY™ C18 column (3.9×150 mm) and eluted by a 85/15 mixture of 50 mM ammonium acetate (pH 4.0) and acetonitrile; the percentage of acetonitrile was increased by a WATERS™ 600E System Controller to 55% over a period of 20 minutes, and then to 100% during the next 10 minutes.

Radiocarbon that eluted from the HPLC was quantified with an on-line radioactivity detector (RADIOMATIC FLO-ONE/BETA™ Radio-Chromatography Detector Series 500 TR Series, Packard Instrument Co.). The peaks of 264W94, 2169W94, and 2169W94 glucuronide were identified by comparing with purified standard compound. Under these conditions, baseline separation of these three components was achieved. The concentration of the three components was determined by normalizing the eluted radioactivity in each peak to the total injected radioactivity.

Data Analysis. Uptake data were normalized to the protein content and expressed as mean ± SD from 3–4 separate preparations of hepatocytes. Statistical differences between mean values for the 10-min cumulative substrate uptake in the presence and absence of Ca$^{2+}$ were determined by the use of the well-known Student's t-test. A P value of <0.05 was considered significant.

In vivo biliary clearance, Cl$_B$ (ml/min/kg body weight), was calculated according to Equation 1:

$$Cl_B = \frac{Amount_{bile(0-T)}}{AUC_{0-T}} \qquad \text{Equation 1}$$

where Amount$_{bile(0-T)}$ represents the amount of parent drug recovered in bile from 0 to time T when most drug was eliminated from the systemic circulation, and AUC$_{0-T}$ represents the area under the plasma concentration-time curve from 0 to time T (in minutes).

The in vivo intrinsic biliary clearance (Cl$_{Bin}$, ml/min/kg body weight) was estimated according to Equation 2 based on the well-stirred model of hepatic disposition assuming biliary excretion is the predominant elimination pathway (Pang et al., J. Pharmacokinet Biopharm. 5:625–653, 1977).

$$Cl_{Bin} \frac{Q \cdot Cl_B}{Q - Cl_B} \qquad \text{Equation 2}$$

where Q represents rat hepatic plasma flow, 40 ml/min/kg of body weight {(blood flow×(1-hematocrit)}; Pollack et al., J. Pharmacol Exp. Ther. 18:197–202, (1989), and Cl$_B$ represents biliary clearance for model compounds reported in the literature or calculated from Equation 1.

Biliary excretion of substrates in the monolayers was quantitatively assessed by the Biliary Excretion Index based on Equation 3:

$$BiliaryExcretionIndex = \frac{Uptake_{standard} - Uptake_{Ca^{++}-free}}{Uptake_{standard}} \cdot 100\%$$ Equation 3 where $Uptake_{standard}$ and $Uptake_{Ca^{++}-free}$ represent the cumulative uptake of substrate over a 10-min interval in the hepatocyte monolayers pre-incubated in standard buffer and in $Ca^{++}$-free buffer, respectively.

Biliary clearance in the sandwich-cultured hepatocytes, $Cl_{B(culture)}$ (ml/min/kg per body weight), was calculated according to Equation 4:

$$Cl_{B(culture)} = \frac{Uptake_{standard} - Uptake_{Ca^{++}-free}}{Time_{incubation} \cdot Concentration_{medium}}$$ Equation 4 where $Time_{incubation}$ was 10 min and $Concentration_{medium}$ represented the initial substrate concentration in the incubation medium. Rat liver weight and protein content in liver tissue were assumed to be 40 g/kg of body weight and 0.20 g/g of liver weight (Seglen et al., Methods in Cell Biology (13$^{th}$ Ed., Prescott D. M. Eds.) pp. 30–78, Academic Press, New York, 1976), respectively, in all calculations.

Summary of the Results of the Examples

Biliary excretion of the five model substrates in long-term sandwich-cultured hepatocytes in accordance with the present invention was consistent with their in vivo biliary excretion properties. Quantification of biliary excretion in the cultured hepatocytes utilizing the biliary excretion index calculation is described hereinabove. Briefly, the biliary excretion index represents the percentage of retained substrate in the bile canaliculi. The results of the Laboratory Examples indicate that compounds undergoing negligible biliary excretion in vivo based on the percentage of dose excreted in bile (e.g., inulin, salicylate) have a low biliary excretion index (approximately zero). Compounds that are more extensively excreted in bile in vivo (e.g., methotrexate, [D-pen$^{2,5}$]enkephalin, and taurocholate) have a high biliary excretion index (approximately 50%).

The relationship between the biliary excretion index and the percentage of the dose excreted in bile in vivo only reveals a categorical correlation. Methotrexate and [D-pen$^{2,5}$]enkephalin represent compounds that are "highly" excreted in bile (approximately 60% and 70% of the i.v. dose was recovered in bile in 1 hr, respectively). In contrast, taurocholate is "rapidly and extensively" excreted in that almost all of the i.v. dose was excreted in bile in less than 1 hr. The biliary excretion index can thus differentiate between compounds that undergo extensive versus negligible or low biliary excretion.

However, the biliary excretion index appears unable to differentiate between compounds that are highly excreted in bile, like methotrexate (biliary excretion index: approximately 55%) or [D-pen$^{2,5}$]enkephalin (biliary excretion index: approximately 42%), and compounds that are "rapidly and extensively" excreted in bile, like taurocholate (biliary excretion index: approximately 56%). This limitation in the biliary excretion index may be due to the fact that this index is determined predominantly by the canalicular excretory functions. The percentage of i.v.-administered substrate excreted into the bile in vivo is dertermined by sinusoidal uptake activity, canalicular excretory activity, as well as other competitive elimination processes.

Biliary clearance represents a more effective parameter for comparison of the relationship between in vivo and in vitro biliary excretion. The in vivo biliary clearance was calculated in the Laboratory Examples as the ratio of the amount excreted into bile at time T and the plasma AUC between time 0 and time T. Because most of the administered dose was eliminated at time T, the biliary clearance approximates the biliary clearance calculated from time 0 to time infinity. Biliary clearance calculated in this matter is a function of intrinsic biliary clearance and the hepatic plasma flow rate. To eliminate the effects of plasma flow, the intrinsic biliary clearance was calculated based on the "well stirred" model of hepatic disposition described by Pang and Rollan in J. Pharmacokinet. Biopharm. 5:625–653, 1977. Likewise, in vitro biliary clearance was calculated as the ratio of the amount excreted in the canalicular networks in the hepatocyte monolayers and the AUC in the incubation medium.

In the sandwich-cultured hepatocytes, the incubation medium was accessible to all hepatocytes in the dish at the same time. Thus, the calculated in vitro biliary clearance should represent the intrinsic biliary clearance. However, since biliary excretion involves two processes, uptake across the sinusoidal membrane and excretion across the canalicular membrane, the true intrinsic biliary clearance should be determined by transport across the canalicular membrane and calculated based on intracellular substrate concentrations. Therefore, the in vivo and in vitro "intrinsic" clearance values calculated in the Laboratory Examples may be referred to as an "apparent" intrinsic biliary clearance value, which would be rate limited by the slowest step in the process, either sinusoidal uptake or canalicular excretion.

The correlation between in vitro biliary clearance and in vivo intrinsic biliary clearance was high ($\Gamma$=0.9865) for the five model substrates. According to the in vivo intrinsic biliary clearance, the five model substrates can be classified into three groups: compounds that are not excreted in bile (inulin and salicylate; approximately 0 ml/min/kg), compounds that are highly excreted in bile (methotrexate and [D-pen$^{2,5}$]enkephalin, approximately 17.3 ml/min/kg and approximately 34.4 ml/min/kg, respectively); and compounds that are rapidly and extensively excreted in bile (taurocholate, approximately 116.9 ml/min/kg). The estimated in vitro biliary clearance adequately differentiated between these three groups of compounds (approximately 0, 4–13, and 56 ml/min/kg, respectively). These results suggest that the biliary clearance more accurately characterizes the relationship between in vivo and in vitro biliary excretion as compared to the biliary excretion index.

EXAMPLE 1

Cumulative Uptake in Cultured Hepatocytes

Figure 1B:
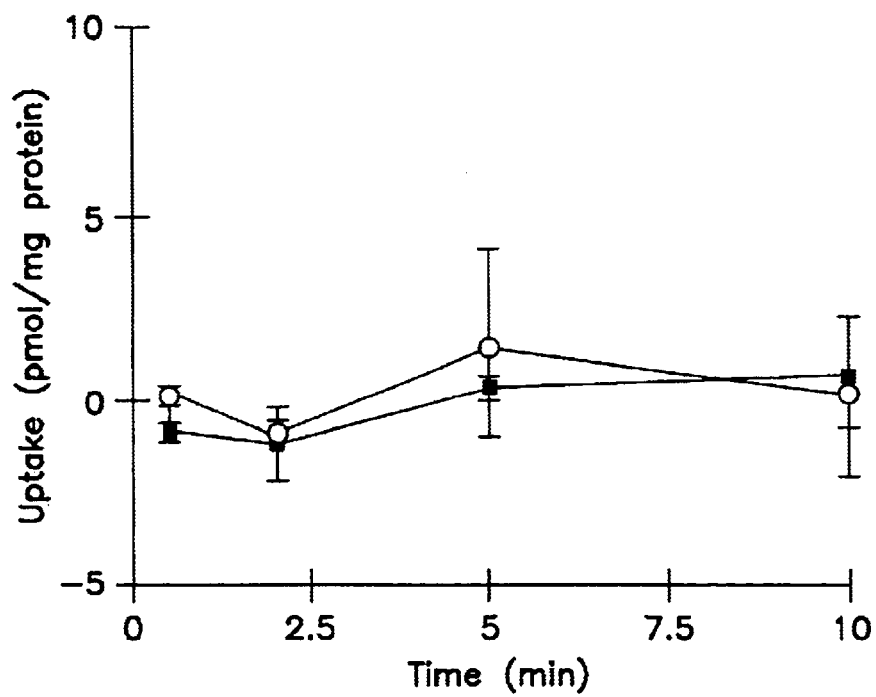
FIG. 1B is a graph depicting cumulative uptake of [$^3$H] inulin (1 $\mu$M) in standard buffer (closed symbols) and $Ca^{++}$-free buffer (open symbols) in hepatocytes cultured in a sandwich configuration for 96 hr.
Figure 2A:
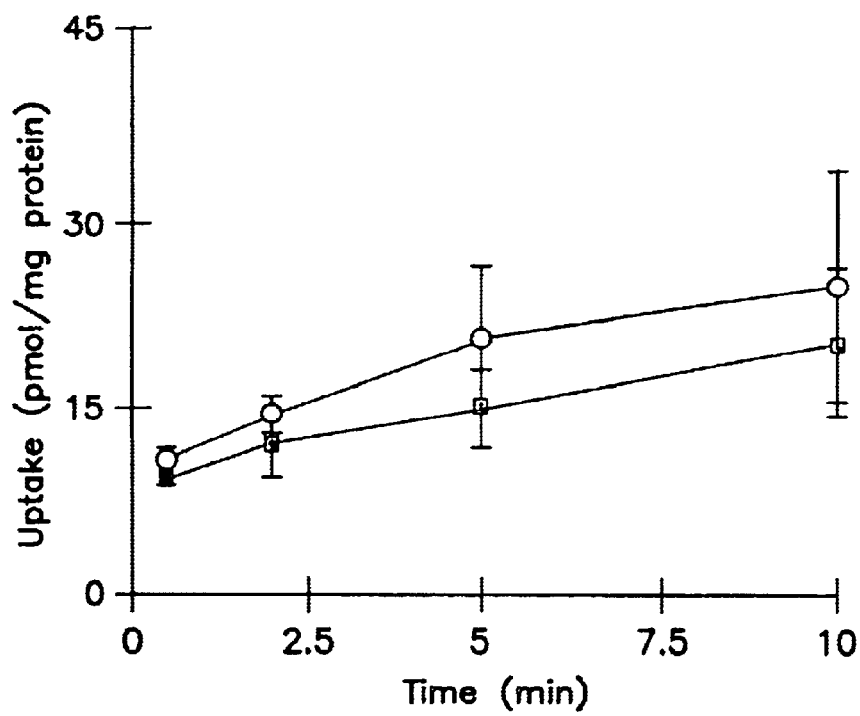
FIG. 2A is a graph depicting cumulative uptake of [$^{14}$C] salicylate (1 $\mu$M) in standard buffer (closed symbols) and $Ca^{++}$-free buffer (open symbols) in hepatocyte monolayers cultured for 3 hr.
Figure 2B:
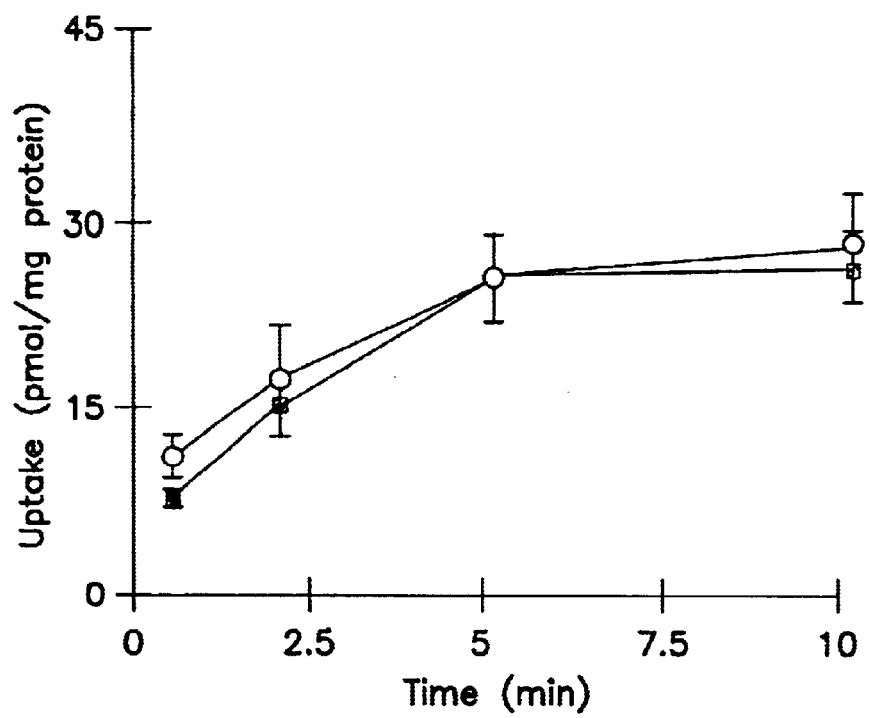
FIG. 2B is a graph depicting cumulative uptake of [$^{14}$C] salicylate (1 $\mu$M) in standard buffer (closed symbols) and $Ca^{++}$-free buffer (open symbols) in hepatocytes cultured in a sandwich configuration for 96 hr.
Figure 3A:
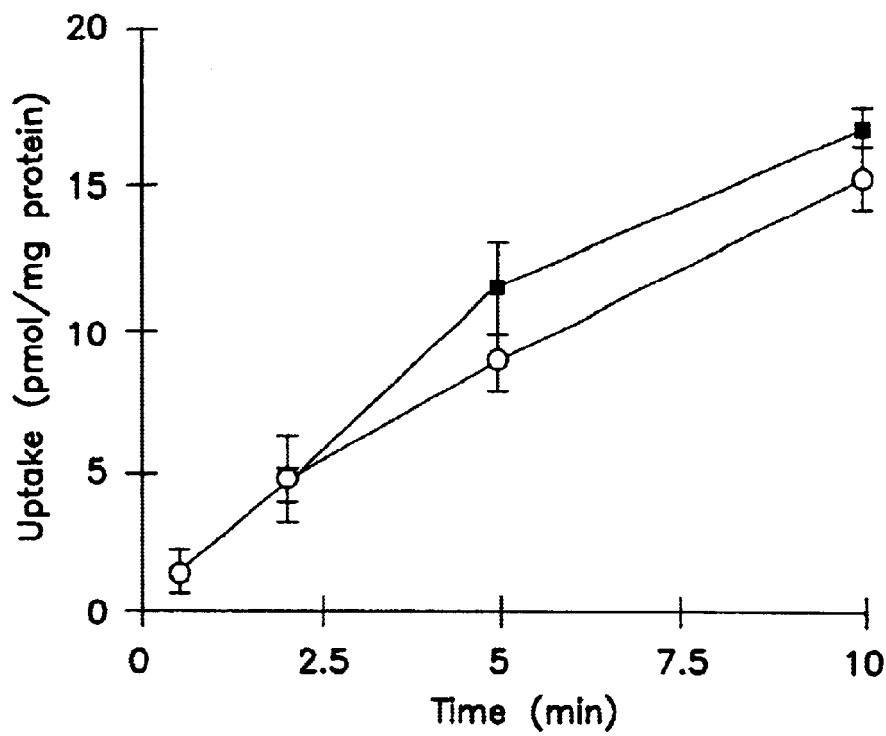
FIG. 3A is a graph depicting cumulative uptake of [$^3$H] methotrexate (1 $\mu$M) in standard buffer (closed symbols) and $Ca^{++}$-free buffer (open symbols) in hepatocyte monolayers cultured for 3 hr.
Figure 3B:
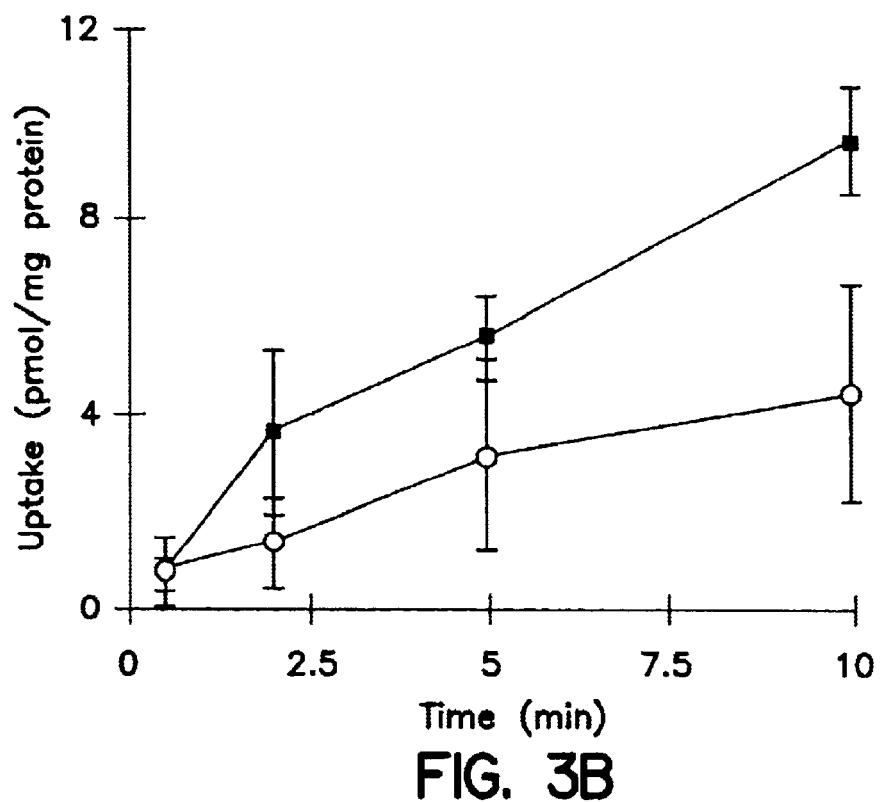
FIG. 3B is a graph depicting cumulative uptake of [$^3$H] methotrexate (1 $\mu$M) in standard buffer (closed symbols) and $Ca^{++}$-free buffer (open symbols) in hepatocytes cultured in a sandwich configuration for 96 hr.
Figure 4A:
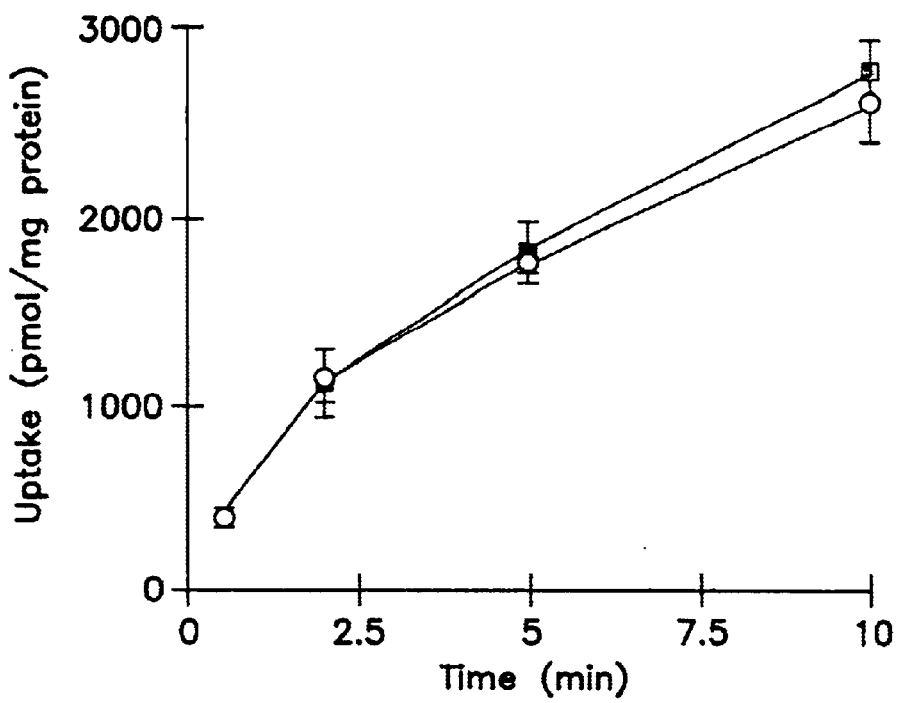
FIG. 4A is a graph depicting cumulative uptake of [$^3$H] [D-pen$^{2,5}$]enkephalin (15 $\mu$M) in standard buffer (closed symbols) and $Ca^{++}$-free buffer (open symbols) in hepatocyte monolayers cultured for 3 hr.
Figure 4B:
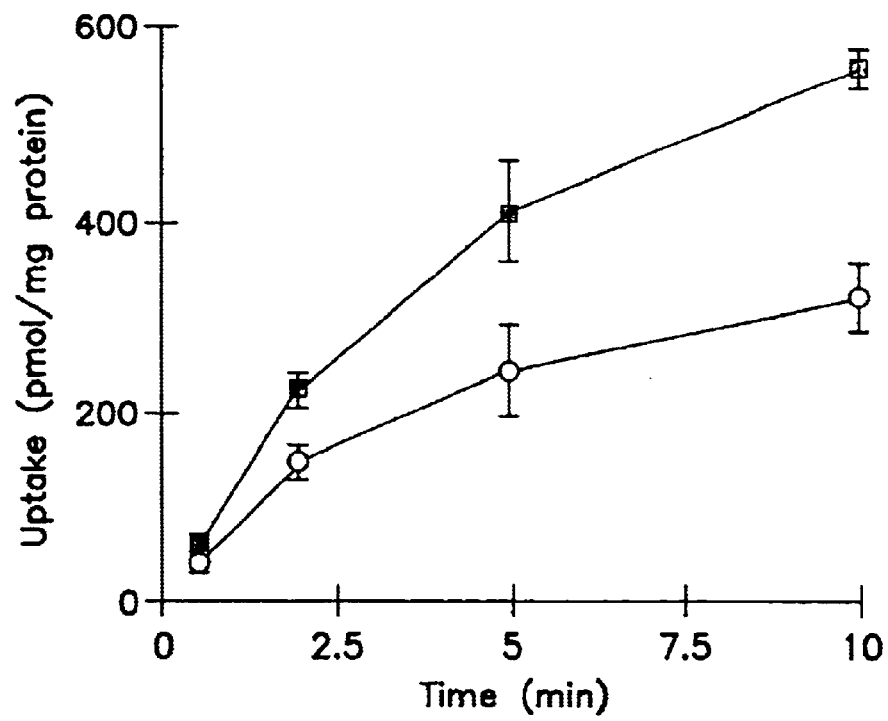
FIG. 4B is graph depicting cumulative uptake of [$^3$H][D-pen$^{2,5}$]enkephalin (15 $\mu$M) in standard buffer (closed symbols) and $Ca^{++}$-free buffer (open symbols) in hepatocytes cultured in a sandwich configuration for 96 hr.
Figure 5A:
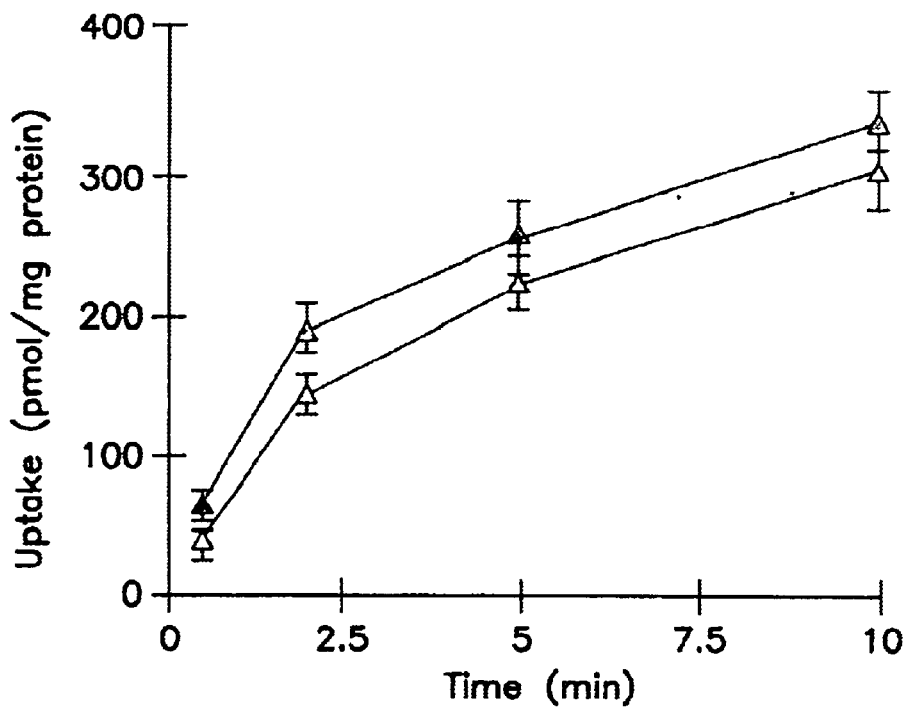
FIG. 5A is a graph depicting cumulative uptake of [$^3$H] tasurocholate (1 $\mu$M) in standard buffer (closed symbols) and $Ca^{++}$-free buffer (open symbols) in hepatocyte monolayers cultured for 3 hr.
Figure 5B:
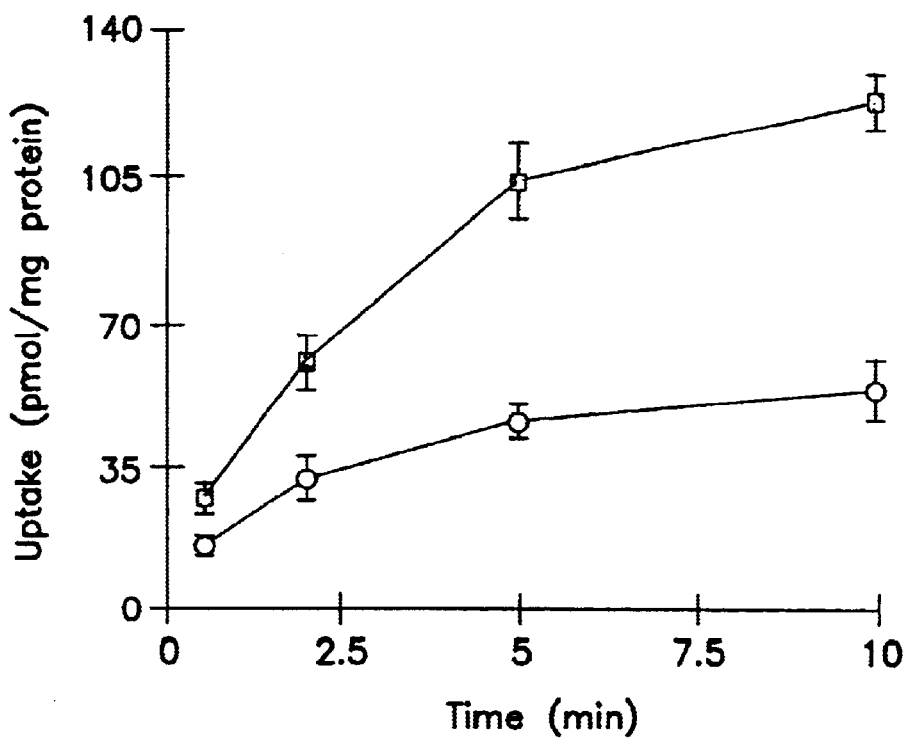
FIG. 5B is a graph depicting cumulative uptake of [$^3$H] taurocholate (1 $\mu$M) in standard buffer (closed symbols) and $Ca^{++}$-free buffer (open symbols) in hepatocytes cultured in a sandwich configuration for 96 hr.

The cumulative uptake of inulin was negligible (less than 0.01% of initial added substrate) at all incubation times in either short-term or long-term cultured hepatocytes (FIGS. 1A and 1B). In the 3-hr cultured hepatocytes, the cumulative uptake of salicylate, methotrexate and [D-pen$^{2,5}$]enkephalin was not significantly different in standard buffer and in $Ca^{2+}$-free buffer (FIGS. 2A, 3A, and 4A; p>0.05). However, slightly higher cumulative uptake of taurocholate in standard buffer compared to $Ca^{2+}$-free buffer was observed (FIG. 5A); at 10 min, the cumulative uptake in standard buffer was approximately 10% higher than in $Ca^{2+}$-free buffer (p=0.0352). In 96-hr cultured hepatocytes, extracellular $Ca^{2+}$ had no effect on the cumulative uptake of salicylate (FIG. 2B, p>0.05). However, the uptake of methotrexate, [D-pen$^{2,5}$]enkephalin, and taurocholate in long-term cultured hepatocytes in standard buffer was significantly higher than in $Ca^{2+}$-free buffer (FIG. 3B, 4B, and 5B; p<0.05).

EXAMPLE 2

Relationship Between the Percentage of Dose Excreted in Bile in Rats And Biliary Excretion Index in Cultured Hepatocytes The five model substrates representing a diverse spectrum of biliary excretion properties were selected to examine the relationship between the percentage of the dose excreted in bile in vivo in rats and the Biliary Excretion Index in sandwich-cultured hepatocytes. Information regarding the percentage of the dose excreted in rat bile after i.v. administration was obtained from the literature. The extent of inulin and salicylate secretion into bile was negligible (Eriksson et al., *Acta. Physiol. Scand.* 95:1–5, 1975; Laznicekand et al., *Eur. J. Drug Met. Pharmacokinet.* 19:21–26, 1994). Approximately 50–60% of a 22 μmol/kg methotrexate dose (Bremnes et al., *Cancer Res.* 49:2460–2464, 1989; Masuda et al., *Cancer Res.* 57:3506–10, 1997) and 70% of a 14.5 μmol/kg [D-pen$^{2,5}$] enkephalin dose (Chen et al., *Pharm. Res.* 14:345–350, 1997) were excreted into rat bile as unchanged drug in 1 hr. Taurocholate biliary excretion was more rapid and extensive than methotrexate and [D-pen$^{2,5}$]enkephalin. In 1 hr, virtually 100% of the dose (8.0 μmol/kg) was recovered in rat bile (Inoue et al., *Biochim. Biophys. Acta.* 833:211–216, 1985).

Figure 6A:
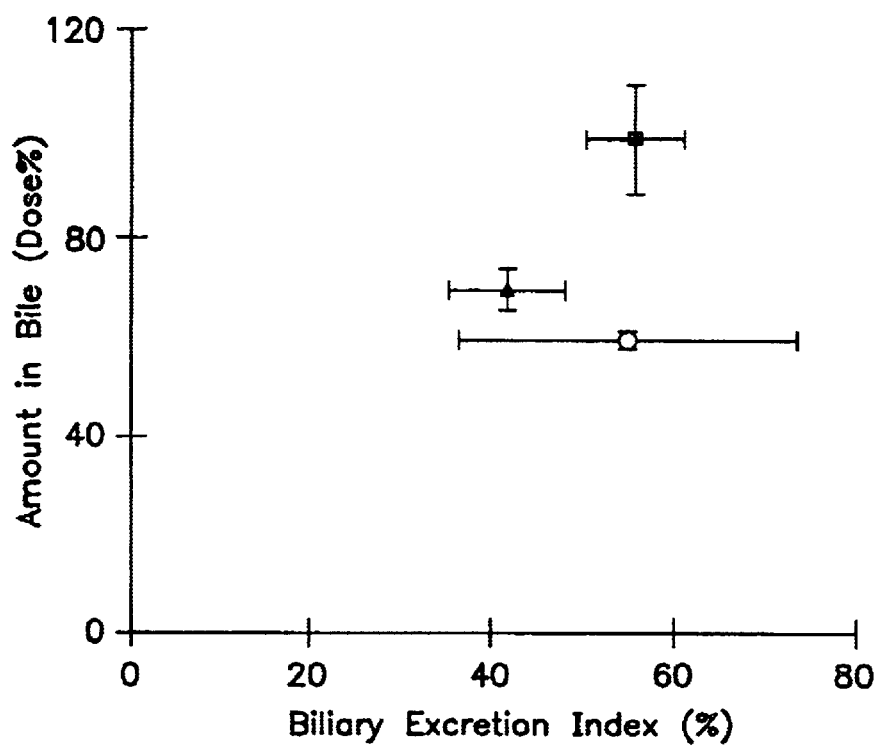
FIG. 6A is a graph depicting the relationship between the percentage of the dose excreted in rat bile in vivo and the Biliary Excretion Index in 96-hr sandwich cultured hepatocytes for the following model substrates: inulin ($\square$), salicylate ($\blacklozenge$), methotrexate ($\bigcirc$), [D-pen$^{2,5}$]enkephalin ($\blacktriangle$), and taurocholate ($\bullet$). The Biliary Excretion Index was calculated from the 10-min cumulative uptake data (FIGS. 1A–5B) based on Equation 3. The broken line is the fit of a linear regression equation to the data.

Biliary excretion in the sandwich-cultured hepatocytes can be expressed quantitatively as the Biliary Excretion Index calculated from Equation 3 based on the 10-min cumulative uptake data in FIGS. 3B–5B. The Biliary Excretion Index of inulin and salicylate was assumed to be negligible because no statistically significant differences in the cumulative uptake of inulin or salicylate were observed between standard buffer and Ca$^{2+}$-free buffer (p>0.05). The Biliary Excretion Index of methotrexate, [D-pen$^{2,5}$] enkephalin and taurocholate was 55.4±18.3%, 42.4±6.5% and 56.4±5.2%, respectively. The relationship between the percentage of the dose excreted in rat bile in vivo and the Biliary Excretion Index measured in the in vitro system is depicted in FIG. 6A. The Biliary Excretion Index was very low for compounds undergoing negligible biliary excretion in vivo (e.g., inulin and salicylate). In contrast, the Biliary Excretion Index was moderately high for compounds that are excreted in bile in vivo (e.g., methotrexate, [D-pen$^{2,5}$] enkephalin, and taurochloate).

EXAMPLE 3

Correlation of In Vitro and In Vivo Biliary Clearance

The in vivo biliary clearance (ml/min per kg body weight) of inulin, salicylate, methotrexate and taurocholate was 0.035 (Utesch et al., *Vitro Cell. Dev. Biol.* 27A:858–863, 1991), ~0 (Laznicekand et al., *Eur. J. Drug Met. Pharmacokinet.* 19:21–26, 1994), 12.1 (Masuda et al., *Cancer Res.* 57:3506–10, 1997), and 29.8 (Inoue et al., *Biochim. Biophys. Acta.* 833:211–216, 1985), respectively. In vivo biliary clearance of [D-pen$^{2,5}$]enkephalin, 18.5 ml/min/kg, was calculated based on Equation 1 from the data reported by Chen and Pollack (Chen and Pollack, *Pharm. Res.* 14:345–350, 1997). Based on these in vivo biliary clearance values, the intrinsic biliary clearance of inulin, salicylate, methotrexate, [D-pen$^{2,5}$]enkephalin and taurocholate was calculated from Equation 2 (0.04, 0. 17.3, 34.4, and 116.9 ml/min/kg, respectively).

Figure 6B:
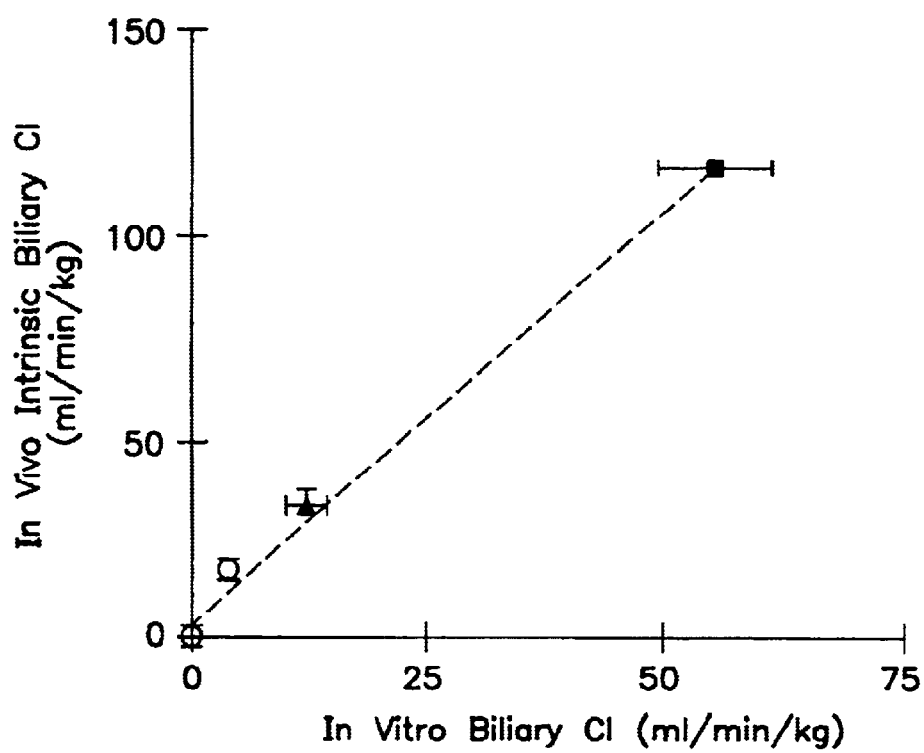
FIG. 6B is a graph depicting the relationship between the percentage of the dose excreted in rat bile in vivo and in vivo intrinsic biliary clearance and in vitro biliary clearance in 96-hr sandwich cultured hepatocytes for the following model substrates: inulin ($\square$), salicylate ($\blacklozenge$), methotrexate ($\bigcirc$), [D-pen$^{2,5}$]enkephalin ($\blacktriangle$), and taurocholate ($\bullet$). The in vivo intrinsic biliary clearance was calculated from Equation 2 based on in vivo biliary clearance values from the literature. The in vitro biliary clearance was calculated from Equation 4. The broken line is the fit of a linear regression equation to the data.

The in vitro biliary clearance of inulin, salicylate, methotrexate, [D-pen$^{2,5}$]enkephalin and taurocholate, calculated from Equation 4 based on the 10-min cumulative uptake data (FIGS. 1B–5B) was ~0, ~0, 4.1±1.0, 12.6±2.2, and 56.2±6.0 ml/min/kg, respectively. The in vivo intrinsic biliary clearance correlated well with the in vitro biliary clearance ($\Gamma^2$=0.9865) for the five model compounds (FIG. 6B).

EXAMPLE 4

Figure 9A:
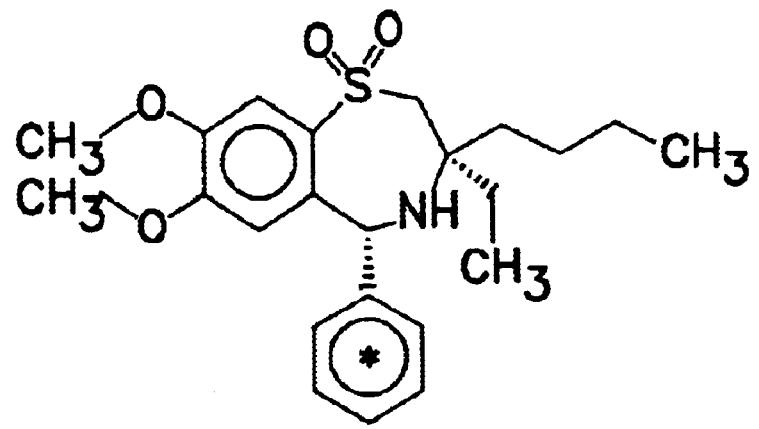
FIG. 9A presents the chemical structures of the compound 264W94, wherein the asterisk sign indicates the position of $^{14}$C incorporated uniformly.
Figure 9B:
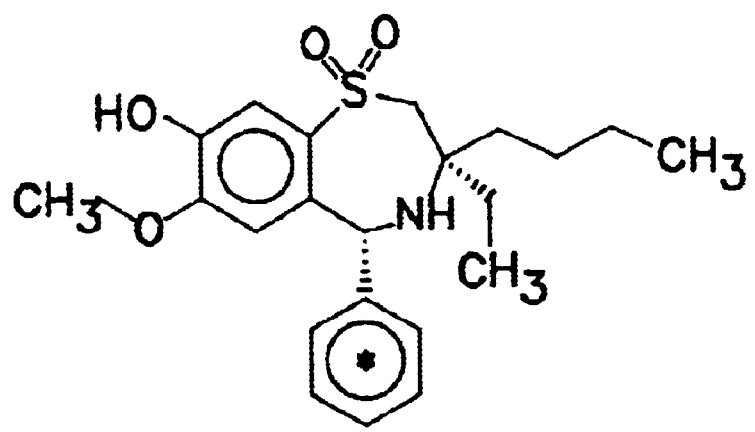
FIG. 9B presents the chemical structures of the compound 2169W94, wherein the asterisk sign indicates the position of $^{14}$C incorporated uniformly.

Comparison of In Vivo and In Vitro Biliary Excretion of 264W94 and its Metabolites The structural formulas of compounds 264W94 and 2169W94 are presented in FIG. 9. Compound 2169W94 is the O-demethylated metabolite of 264W94 in rats and humans, which can undergo further conjugation with urindine-5'-diphosphoflucuronic acid to form a glucuronide conjugate (Silver et al., *ISSX Proceedings,* (San Diego, Calif. USA) pp. 387, 1996).

After i.v. administration of [$^{14}$C]264W94 to rats (0.24 μmol/kg), neither 264W94 nor 2169W94 was detected in bile in 24 hr. However, 35.4% (n=2) of the total administered radioactivity was recovered in bile in the first hour. Approximately, 30.0% of the radioactivity recovered in bile was the 2169W94 glucuronide; the remaining 70% of radioactivity in bile represented unidentified metabolites. After oral administration of [$^{14}$C]264W94 to rats (2.4 μmol/kg), 2169W94 was not detected in the bile in 24 hr. However, 66.4% (n=2) of the total administered radioactivity was recovered in bile in 8 hr. Approximately, 88.7% of the radioactivity in bile was in the form of the 2169W94 glucuronide conjugate. These in vivo results demonstrate that 264W94 and its O-demethylated product, 2169W94, undergo negligible biliary excretion, but the glucouronide conjugate of 2169W94 undergoes extensive biliary excretion in rats.

Figure 7A:
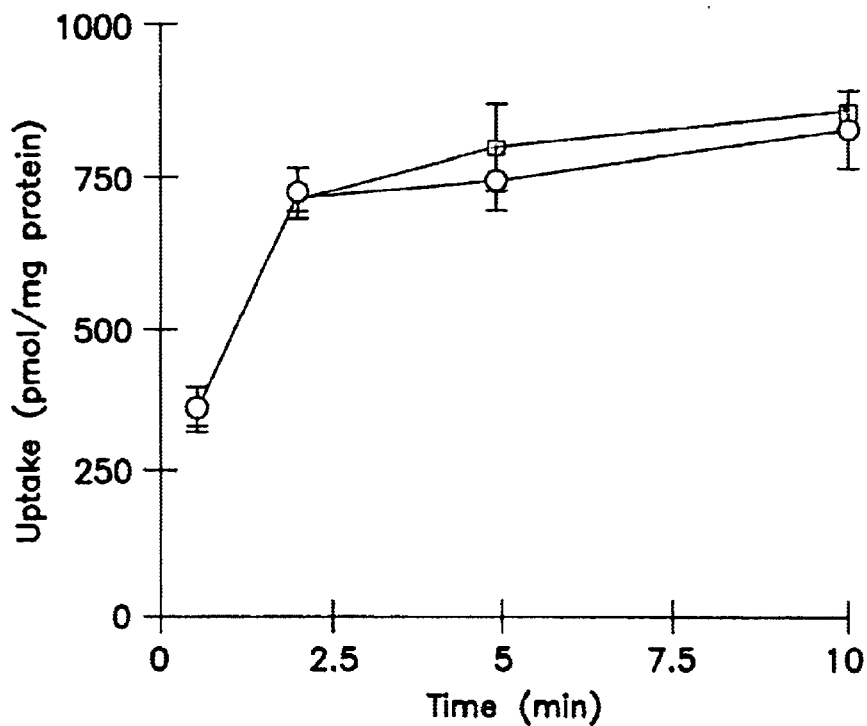
FIG. 7A is a graph depicting cumulative uptake of [$^3$H] 264W94 (3 $\mu$M) in standard buffer (closed symbols) and $Ca^{++}$-free buffer (open symbols) in hepatocyte monolayers cultured for 3 hr.
Figure 7B:
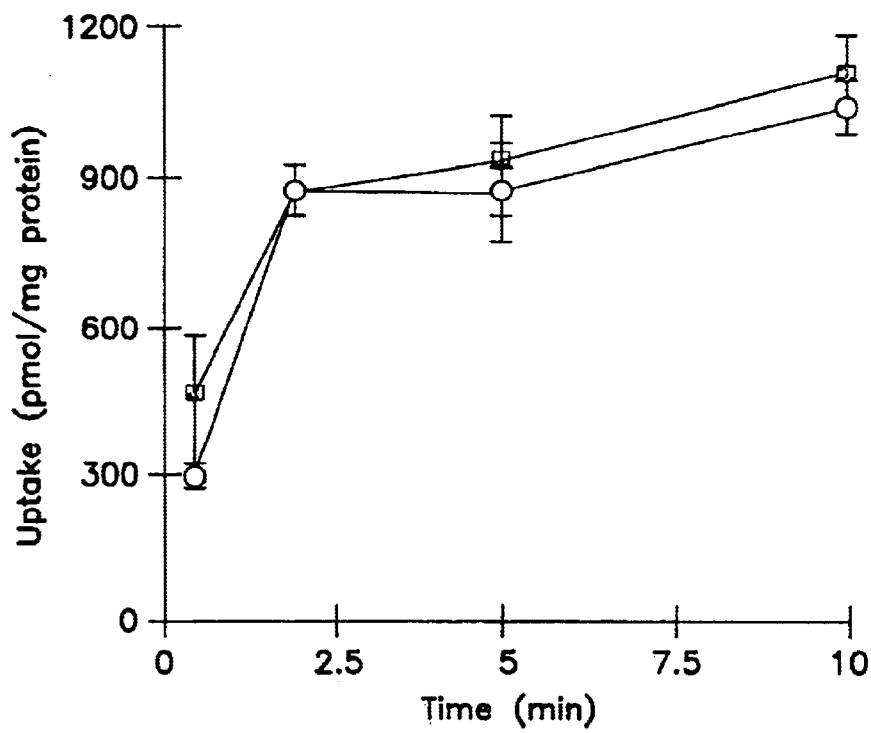
FIG. 7B is a graph depicting cumulative uptake of [$^3$H] 264W94 (3 $\mu$M) in standard buffer (closed symbols) and $Ca^{++}$-free buffer (open symbols) in hepatocytes cultured in a sandwich configuration for 96 hr.
Figure 8A:
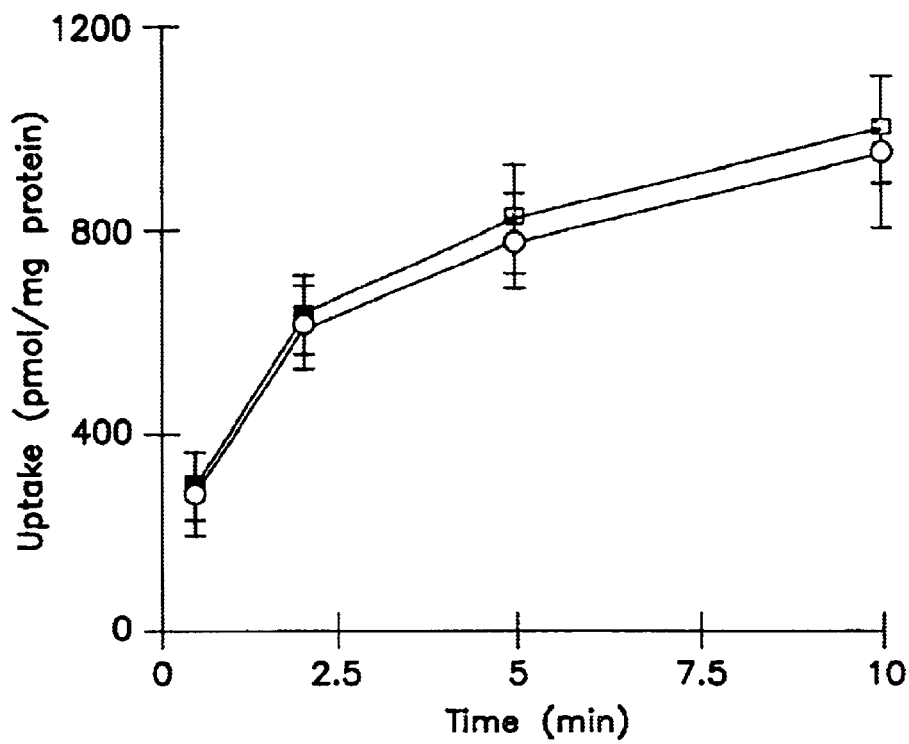
FIG. 8A is a graph depicting cumulative uptake of [$^3$H] 2169W94 (3 $\mu$M) in standard buffer (closed symbols) and $Ca^{++}$-free buffer (open symbols in hepatocyte monolayers cultured for 3 hr.

To determine the biliary excretion of 264W94 and metabolites in 3-hr and 96-hr cultured hepatocytes, hepatocyte monolayers were incubated in standard or Ca$^{2+}$-free buffer before cumulative uptake was conducted in standard buffer containing 3 μM of [$^{14}$C]264W94 or [$^{14}$C]2169W94 (FIG. 7 and 8). In 3-hr cultured hepatocytes, the cumulative uptake measured by total radioactivity of 264W94 or 2169W94 was similar in the hepatocytes pre-incubated in standard buffer or Ca$^{2+}$-free buffer (p>0.05), suggesting that the uptake of 264W94 and 2169W94 in short-term cultured hepatocytes was not affected by pre-incubation of the monolayers in Ca$^{2+}$-free buffer. In 96-hr cultured hepatocytes, the 1 0-min cumulative uptake of 264W94 measured by total radioactivity was not significantly different in the monolayers pre-incubated in standard buffer or Ca$^{2+}$-free buffer (p>0.05).

HPLC analysis of the cell lysate at 10 min revealed that 73.0% of the total radioactivity was in the form of 264W94 and 3.3% was the 2169W94 glucuronide conjugate; 2169W94 was not detected in the lysate. In 96-hr sandwich-cultured hepatocytes, 10-min cumulative uptake of 2169W94 was approximately 70% greater in the presence of Ca$^{2+}$ than in the absence of Ca$^{2+}$ (p>0.05). In the 10-min cell lysate, approximately 16.7% of total radioactivity was in the form of 2169W94, and approximately 58.5 was the 2169W94 glucuronide conjugate. Compound 2169W94 forms the glucuronide conjugate which is excreted into bile canalicular networks in long-term cultured hepatocytes.

To further characterize the utility of the in vitro biliary excretion assay of the present invention to predict in vivo biliary excretion of drug metabolites, the in vitro and in vivo biliary excretion of 264W94, and its O-demethylated metabolites 269W694 and 2169W94 glucuronide were examined. Previous in vitro studies conducted with rat and human liver microsomes, precision cut liver slices, and cDNA expressed hepatic cytochrome p450 isozymes indicated that 264W94 formed an O-demethylated metabolite at the 8-methoxy position. Among the several cytochrome p450 isozymes examined, CYP3A4 was the isozyme primarily involved in the metabolism of 264W94 (Silver et al., *ISSX Proceedings* (San Diego, Calif. USA) p. 387, 1996).

In vivo disposition studies demonstrated that neither 264W94 nor its O-demethylated metabolite, 2169W94, was excreted in the bile. But, the 2169W94 glucuronide conjugate, along with other unidentified metabolites, were extensively excreted in bile. The lack of biliary excretion of 264W94 in long-term sandwich-cultured hepatocytes was consistent with negligible in vivo biliary excretion of 264W94.

In vivo, approximately 35% of 264W94 equivalent was excreted in bile as metabolites in 1 hr after i.v. administration of 264W94. In cultured hepatocytes, however, the biliary excretion of 264W94 metabolites was negligible (FIG. 7B). This apparent discrepancy between the in vivo and in vitro biliary excretion for metabolites of 264W94 may be explained by differences in metabolic activities. In vivo, 264W94 undergoes O-demethylation to form 2169W94; and subsequently, 2169W94 is conjugated with uridine-5'-diphosphoglucuronic acid to form 2169W94 glucuronide. This glucuronide conjugate accounts for 30% of the total amount excreted in bile. In the lysate of long-term sandwich-cultured hepatocytes incubated with 264W94, only approximately 3% of the total amount incubated was detected as the 2169W94 glucuronide conjugate. These results indicated that the long-term cultured hepatocytes were not capable of the O-demethylation reaction. Consequently, negligible glucuronide conjugate was formed and excreted in the bile.

Figure 8B:
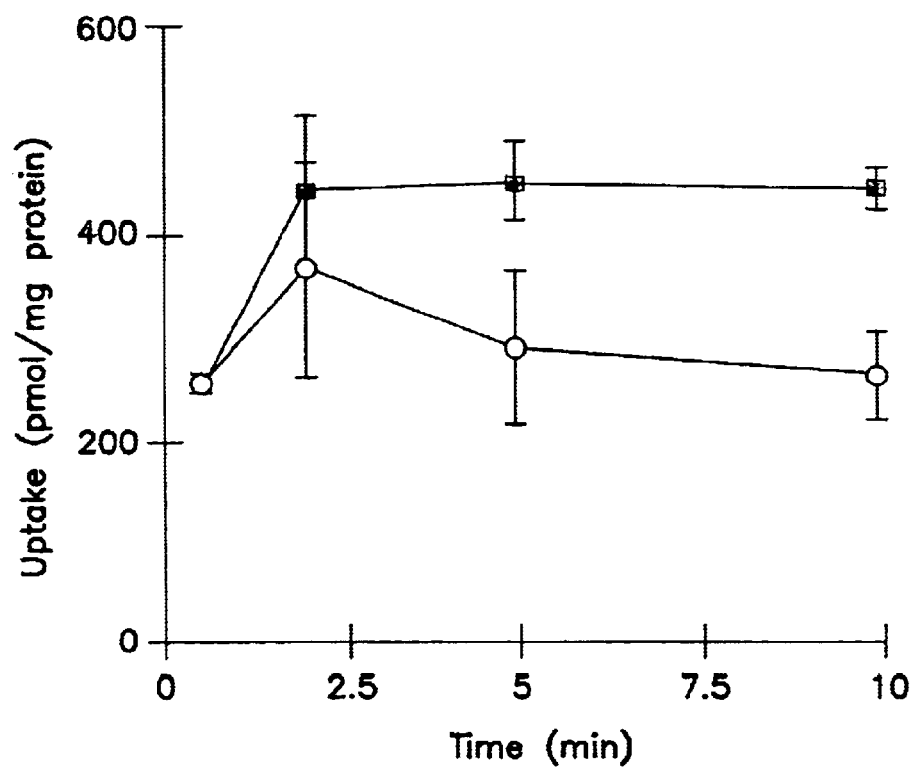
FIG. 8B is a graph depicting cumulative uptake of [$^3$H] 2169W94 (3 $\mu$M) in standard buffer (closed symbols) and $Ca^{++}$-free buffer (open symbols) in hepatocytes cultured in a sandwich configuration for 96 hr.

However, after incubation of the monolayers with 2169W94, the O-demethylated metabolite of 264W94, 58.5% of 2169W94 was converted to glucuronide conjugates and significant biliary excretion was observed in the cultured hepatocytes (FIG. 8B). Evidently, phase I metabolic activities such as O-demethylation deteriorate significantly, while the phase II metabolic activities such as glucuronide conjugation are maintained, at least in part, in the long-term sandwich-cultured hepatocytes used in accordance with the present invention. Thus, this Laboratory Example further indicates that the assay of the present invention can be employed to predict in vivo biliary excretion of a substrate in its parent form. Indeed, the application of the present in vitro assay method to study and to predict in vivo biliary excretion of metabolites requires consideration of the status of metabolic activities in the monolayers.

References

The references listed below as well as all references cited in the specification are incorporated herein by reference to the extent that they supplement, explain, provide a background for or teach methodology, techniques and/or compositions employed herein.

Boyer and Soroka, *Gastroenterology* 109:1600–1611, 1995
Bremnes et al., *Cancer Res.* 49:2460–2464, 1989.
Chen et al., *Pharm. Res.* 14:345–350, 1997.
Dunn et al., *FASEB J.* 3:174–177, 1989.
Eriksson et al., *Acta. Physiol. Scand.* 95:1–5, 1975.
Haugland, *Molecular Probes: Handbook of Fluorescent Probes and Research Chemicals* (1992–1994), p. 134, Molecular Probes, Inc., 1992.
Inoue et al., *Biochim. Biophys. Acta.* 833:211–216, 1985.
Laznicekand et al., *Eur. J. Drug Met. Pharmacokinet.* 19:21–26, 1994.
LeCluyse et al., *Am. J. Physiol.* 266(Cell Physiol. 35):C1764–1774, 1994.
LeCluyse et al., *Cultured rat hepatocytes, in Models for Assessing Drug Absorption and Metabolism* (Borchard et al. eds), pp 121–160, Plenum Press, New York, 1996.
Liu et al., *Pharm. Res. Init.* 13:S-393 (8003), 1996.
Liu et al., *Hepatology* 24:370A (973), 1996.
Liu et al., *Pharm. Res.* 24:S-459 (3007),1997.
Liu et al., *Hepatology* 26:297A (675), 1997.
Liu et al., *Pharm. Sci.* 1:S-119, 1998.
Liu et al., *Pharmaceutical Research,* 15:1533–1539, 1998.
Masuda et al., *Cancer Res.* 57:3506–10, 1997.
Pang et al., *J. Pharmacokinet Biopharm.* 5:625–653, 1977.
Parkinson, A., *Biotransformation of Xenobiotics in Casarett and Doull's Toxicology. The Basic Science of Poisons.,* $5^{th}$ Ed. (Klaassen, C. D. ed.) pp.113–186, McGraw Hill, New York, 1996.
Pollack et al., *J. Pharmacol. Exp. Ther.* 18:197–202, 1989.
Seglen, Methods in Cell Biology($13^{th}$ Ed., Prescott D. M. Eds.) pp. 30–78, Academic Press, New York, 1976.
Sidhu et al., *Pharmacogenetics* 5:24–36, 1993.
Silver et al., *ISSX Proceedings* (San Diego, Calif. USA) pp. 387, 1996.
Utesch et al., *In Vitro Cell Dev. Biol.* 27A:858–863, 1991.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of screening a xenobiotic for susceptibility to biliary excretion, the method comprising the steps of:
   (a) establishing first and second cultures of hepatocytes, each culture comprising at least one bile canaliculus, the first culture having intact bile canaliculi and the second culture having disrupted bile canailculi;
   (b) exposing a xenobiotic to the first culture and to the second culture for a time (T) sufficient to allow uptake of the xenobiotic;
   (c) washing and then lysing the first and second cultures;
   (d) measuring an amount of xenobiotic present in a lysate obtained from each culture in step (c);
   (e) calculating a mass in the bile canaliculi as the difference in the amount of xenobiotic present in the lysates from the first culture having intact bile canaliculi and the second culture having disrupted bile canaliculi; and
   (f) calculating a biliary clearance value as the ratio of the mass in the bile canaliculi in step (e) and the area under the curve (AUC) in culture medium, wherein the AUC represents the inteqral of xenobiotic concentration in the medium from time 0 to time T, to thereby screen the xenobiotic for susceptibility to biliary excretion.

2. The method of claim 1, wherein the hepatocytes are isolated from a source selected from the group consisting of rat, human, monkey, ape, cat, dog, pig, hog, cattle, oxen, sheep, horses, turkeys, chickens, ducks and geese.

3. The method of claim 1, wherein the first and second cultures of hepatocytes each further comprise a long-term culture of hepatocytes.

4. The method of claim 1, wherein the first and second cultures of hepatocytes further comprise a canalicular network.

5. The method of claim 1, wherein the first and second cultures of hepatocytes are further characterized as having a configuration selected from the group consisting of clusters of hepatocytes, aggregates of hepatocytes, at least one layer at hepatocytes, and combinations thereof.

6. The method of claim 1, wherein the hepatocytes are embedded in a matrix.

7. The method of claim 1, wherein the first and second cultures of hepatocytes further comprise a sandwich culture of hepatocytes, the sandwich culture comprising at least one layer of hepatocytes and at least one bile canaliculus with the at least one layer of hepatocytes.

8. The method of claim 7, wherein the at least one layer of hepatocytes is sandwiched between two layers of matrix.

9. The method of claim 7, wherein the first and second cultures of hepatocytes each further comprise a long-term culture of hepatocytes.

10. The method of claim 6, wherein the matrix is selected from the group consisting of a biological matrix medium, a synthetic matrix medium, and combinations thereof.

11. The method of claim 10, wherein the biological matrix medium is selected from the group consisting of collagens, laminins, basement membrane-derived complexes, derivatives thereof and combinations thereof.

12. The method of claim 1, wherein steps (a) through (d) are carried out in at least one well of a multi-well plate.

13. The method of claim 1, further comprising screening a plurality of xenobiotics simultaneously for susceptibility to biliary excretion.

14. The method of claim 1, further comprising the step of differentiating between a xenobiotic that is not excreted in bile, a xenobiotic that is highly excreted in bile, and a xenobiotic that is readily and extensively excreted in bile.

* * * * *